United States Patent [19]

Holstedt et al.

[11] Patent Number: 4,511,516

[45] Date of Patent: Apr. 16, 1985

[54] BORON CONTAINING HETEROCYCLIC COMPOUNDS

[75] Inventors: Richard A. Holstedt, Whittier; Kenneth Baron, Diamond Bar; Peter Jessup, Santa Ana, all of Calif.

[73] Assignee: Union Oil Company of California, Los Angeles, Calif.

[21] Appl. No.: 418,196

[22] Filed: Sep. 15, 1982

Related U.S. Application Data

[63] Continuation-in-part of Ser. No. 158,828, Jun. 12, 1980, Pat. No. 4,400,284, and a continuation-in-part of Ser. No. 158,981, Jun. 12, 1980.

[51] Int. Cl.³ .......................... C07F 5/04; C10M 3/48
[52] U.S. Cl. ................................. 260/462 R; 564/8; 564/475; 252/49.6
[58] Field of Search ................ 252/49.6; 260/462 R; 564/8, 475

[56] References Cited

U.S. PATENT DOCUMENTS

| | | | |
|---|---|---|---|
| 2,441,063 | 5/1948 | Gilman | 260/462 R |
| 2,987,476 | 6/1961 | Hartley et al. | 252/49.6 |
| 3,185,644 | 5/1965 | Knowles et al. | 252/49.6 |
| 3,224,971 | 12/1965 | Knowles et al. | 260/462 R |
| 3,227,739 | 1/1966 | Versteeg | 260/462 |
| 3,269,853 | 8/1966 | English | 260/462 R |
| 3,313,727 | 4/1967 | Peeler | 252/49.6 |
| 3,429,909 | 2/1969 | Schuster | 260/462 R |
| 3,574,755 | 4/1971 | McConnell et al. | 564/475 |
| 3,598,757 | 8/1971 | Cyba | 252/400 |
| 3,598,855 | 8/1971 | Cyba | 260/462 R |
| 3,642,652 | 2/1972 | Birgy | 260/462 R |
| 3,658,836 | 4/1972 | Vineyard | 564/8 |
| 3,697,574 | 10/1972 | Piasek et al. | 564/8 |
| 3,764,593 | 10/1973 | Schuster | 260/462 R |
| 3,775,480 | 11/1973 | Glasby | 564/475 |
| 4,074,013 | 2/1978 | Kock et al. | 564/475 |
| 4,136,039 | 1/1979 | Jäger | 260/462 R |
| 4,176,076 | 11/1979 | Waldstein | 252/49.6 |
| 4,181,624 | 1/1980 | Kock | 564/475 |
| 4,204,972 | 5/1980 | Knoblauch et al. | 260/462 R |
| 4,226,734 | 10/1980 | Schuster | 252/49.3 |
| 4,382,006 | 5/1983 | Horodysky | 252/49.7 |
| 4,406,802 | 9/1983 | Horodysky et al. | 252/49.6 |

OTHER PUBLICATIONS

Morrison & Boyd, *Organic Chemistry*, 1966, p. 66.
*Condensed Chemical Dictionary*, 7th edition, Reinbold Pub. Comp., pp. 31–32.
Weast, *Handbook of Chemistry and Physics*, 61th edition, section C-1, para. 1.2.
U.S. Application No. 91,903, filed Nov. 6, 1979 to Horodysky.

*Primary Examiner*—Glennon H. Hollrah
*Assistant Examiner*—Raymond Covington
*Attorney, Agent, or Firm*—Dean Sandford; Gregory F. Wirzbicki; Cleveland R. Williams

[57] ABSTRACT

Boron-containing heterocyclic compounds of the chemical formula:

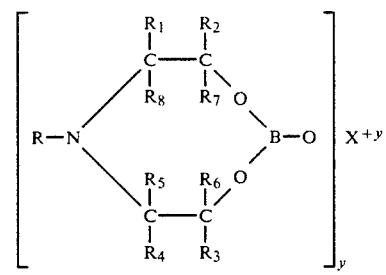

wherein at least one of $R_1$, $R_2$, $R_3$, or $R_4$ is an aryl, alkylaryl, or arylalkyl radical having from 1 to about 30 carbon atoms have been found useful as extreme pressure, anti-wear and friction-reducing additives for lubricating oils. The boron-containing heterocyclic compounds of the present invention are the reaction product of boric acid with the intermediate reaction product of a primary amine and an aromatic oxide. Metal derivatives of the boron-containing heterocyclic compounds are obtained by chemical reaction with a metal or compound thereof, particularly a first row transition metal or a Group IVA metal, or a compound thereof.

24 Claims, No Drawings

BORON CONTAINING HETEROCYCLIC COMPOUNDS

RELATED APPLICATIONS

This application is a continuation-in-part of copending application Ser. No. 158,828 now U.S. Pat. No. 4,400,284 and Ser. No. 158,981, both applications filed on June 12, 1980.

BACKGROUND OF THE INVENTION

This invention relates to new boron-containing heterocyclic compounds, metal derivatives thereof, and methods for producing the compounds and metal derivatives. The invention further relates to lubricating oils and additives for use therein, and particularly to lubricating oils containing extreme pressure, anti-wear and friction-reducing additives.

Anti-wear, friction reducing and extreme pressure or "E.P." additives, as they are commonly called, are chemicals which are added to lubricating compositions to reduce friction and reduce or prevent destructive metal-to-metal contact in the lubrication of moving surfaces. Lubricating oils provide good lubrication between moving surfaces in contact with each other, as long as a film of said oil is maintained between the relatively moving surfaces. This particular kind of lubrication is commonly termed "hydrodynamic lubrication". However, when pressure and/or rubbing speeds between moving metal surfaces are such that the film of lubricating oil is no longer intact, metal-to-metal contact and wear occur over a significant portion of the previously lubricated area. Destructive metal-to-metal contact, due to lack of lubrication under extreme conditions, manifests itself in different forms such as scoring, welding, scuffing, ridging, rippling, rapid wear, and in some cases deformation or complete destruction of the metal components.

Extreme pressure, anti-wear and friction reducing lubricating additives prevent destructive metal-to-metal contact, under boundary lubrication conditions, by adsorption or reacting with relatively moving metal surfaces to form an adherent, protective film of compounds. This film acts in the capacity of a "boundary lubricant" and performs the function of lubrication when metal-to-metal contact occurs. Boundary conditions and boundary lubricant refer to the conditions and a suitable lubricant relating to the combination of applied load, fluid viscosity and rubbing speed, which do not allow hydrodynamic lubrication to exist. Hydrodynamic lubrication exists when a film of lubricant maintains separation between lubricated surfaces.

Many extreme pressure and anti-wear agents are oil soluble or easily dispersed as a stable dispersion in oil. Many of the E.P. agents which provide high load capacity are chemically reactive, containing chlorine, sulfur or phosphorus which react with metal surfaces.

It has now been discovered that certain oil-soluble or dispersible boron or metal-boron derivatives prepared as described herein, when added to lubricating oils or grease not only improve the ability of the lubricant to prevent seizure of the parts being lubricated but in addition greatly reduce the amount of friction and wear of such moving parts. Thus, a new family of extreme pressure and anti-wear compounds which are boron derivatives and/or reaction products of boron derivatives and metal salts thereof have been synthesized as described further herein.

It is well recognized in the petroleum industry that boron containing compounds are desirable additives for lubricating oils. One such boron containing compound is disclosed in U.S. Pat. No. 3,224,971 to Knowles et al. which relates to intracomplexed borate esters and to lubricating compositions containing said esters. The borate esters are organo-boron compounds derived from boric acid and a bis(o-alkylphenyl) amine or sulfide. These compounds are described as additives for lubricating oils.

Another boron ester composition is described in U.S. Pat. No. 3,269,853 to English et al. which discloses a boron ester curing agent which consists of a cyclic ring structure containing boron, oxygen, nitrogen, carbon and hydrogen.

It is an object of the present invention to provide a novel boron containing heterocyclic compound having extreme pressure, anti-wear and friction reducing properties for use in lubricating oils.

Another object of the invention is to provide a method of producing boron containing heterocyclic compounds.

Yet another object of the invention is to provide an improved lubricating oil having improved extreme pressure, anti-wear and friction reducing properties.

Other objects and advantages of the invention will be apparent from the following description.

SUMMARY OF THE INVENTION

Boron containing heterocyclic compounds of the present invention have the formula:

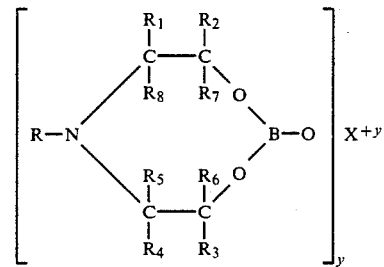

where R is hydrogen or an alkyl, alkene, alkadiene, aryl, alkylaryl or arylalkyl radical having from 1 to 24 carbon atoms, $R_1$, $R_2$, $R_3$ and $R_4$ are the same or different radicals selected from hydrogen or an alkyl, aryl, alkylaryl or arylalkyl radicals having from 1 to about 30 carbon atoms, wherein at least one of said $R_1$, $R_2$, $R_3$ or $R_4$ is an aryl, alkylaryl or arylalkyl radical having from about 6 to about 30 carbon atoms, $R_5$, $R_6$, $R_7$ and $R_8$ are the same or different radicals selected from hydrogen or an alkyl group having from 1 to about 6 carbon atoms, y is an integer between 1 and 4, and x is hydrogen or a metal selected from a transition metal having an atomic number of 21 through 30 or a Group IVA metal.

The boron-containing heterocyclic compounds are produced by (A) reacting a primary amine with an aromatic oxide of the formula:

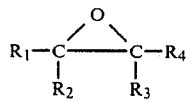

wherein at least one of said $R_1$, $R_2$, $R_3$ or $R_4$ is aryl, alkylaryl or arylalkyl with the remaining R groups being independently hydrogen or an organic radical having 1 to 30 carbon atoms, preferably hydrogen or an alkyl radical having 1 to 6 carbon atoms to form a reaction product, and (B) reacting the reaction product of step (A) with boric acid to form a boramid compound. The boramid compound thus formed may be reacted with a transition metal having an atomic number of 21 through 30 or a Group IVA metal of the periodic Table or salt thereof to produce a metal-boron compound.

The above-described, boron containing heterocyclic compounds impart extreme pressure, anti-wear and friction reducing properties to lubricating oils when added to said oils at use concentrations.

DETAILED DESCRIPTION OF THE INVENTION

The present invention resides in novel boron-containing heterocyclic compounds, metal derivatives of said compounds, and in the manufacture and use of such compounds. The boron-containing heterocyclic compounds of this invention are referred to herein as boramid compounds and metal boramid compounds. The boramid compounds of this invention are conveniently prepared by reacting a primary amine with boric acid and certain aromatic oxides described in greater detail hereinafter. The metal boramid compounds are conveniently produced by reacting boramid compounds with a transition metal, Group IVA metal or a compound thereof.

Primary amines useful in preparing the boramid compounds and metal boramid compounds of this invention are obtainable commercially or may be produced by reacting alkyl, aryl, alkylaryl or arylalkyl halides with ammonia using conventional techniques and apparatus. These halides react with ammonia at moderately high temperatures and under pressure to produce a mixture of primary, secondary and tertiary amines. The primary amine yield of this process may be improved by using an excess of ammonia in the reaction.

Another typical process for producing primary amines consists of reacting alcohols with ammonia in the vapor phase at temperatures of from 570° F. to 940° F. under 200 to 1,000 p.s.i.g. For the lower molecular weight alcohols, temperatures of 750° F., pressures of about 200 p.s.i.g. and a reaction time of 2 to 3 hours are desirable. The alcohols and ammonia may be conveniently obtained from commercial sources. A mixture of primary, secondary and tertiary amines is formed wherein the amines exist in equilibrium with each other. It is possible to improve the yield of the desired amine by recycling undesired amines through the vapor phase. However, the most convenient method of obtaining the desired primary amine is through commercial sources.

Unsaturated primary amines are conventionally prepared by reacting a fatty acid with ammonia to produce an ammonium soap. The ammonium soap is heated to produce an amide. The amide thus produced is heated in the presence of a standard dehydration catalyst to produce a nitrile. The nitrile is contacted with hydrogen gas at increased temperature to produce either an unsaturated amine or a saturated amine depending upon the degree of hydrogenation the nitrile is subjected to.

Primary amines useful in preparing the boramid compounds of the present invention have the chemical formula $RNH_2$ wherein R is an organic radical, preferably where R contains no more than 30 carbon atoms. Among the suitable amines are methyl amine, ethylamine, propylamine, butylamine, octadecyl amine, cyclohexylamine, dodecylamine, phenylamine, oleylamine, cocoamine and tallowamine and mixtures thereof.

In preparing the boramid compounds, these primary amines are reacted with an aromatic oxide to produce an aryl-oxylated primary amine. Alternatively, ammonia may be reacted with the aromatic oxide. Aromatic oxides suitable for use herein have the formula:

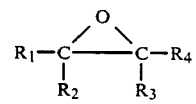

wherein at least one of said $R_1$, $R_2$, $R_3$ or $R_4$ is aryl, alkylaryl or arylalkyl with the remaining R groups being independently hydrogen or an organic radical having 1 to 30 carbon atoms, preferably hydrogen or an alkyl radical having 1 to 6 carbon atoms.

Suitable aromatic oxides may be obtained from a commercial source or prepared by three general methods: (1) direct oxidation of aromatic olefins in the presence of a conventional oxidation catalyst; (2) reaction of aromatic olefins with peroxy acids; and (3) hydrolysis of chlorohydrins with bases.

A wide variety of aromatic oxides may be used to prepare the aryl-oxylated primary amines needed to produce the boramid compounds herein. Typical aromatic oxides for use herein include styrene oxide, alpha methyl styrene oxide, para tertiary butyl styrene oxide, cresyl oxide including ortho methyl styrene oxide and para methyl styrene oxide and mixtures thereof.

The primary amine is normally reacted with the aromatic oxide in the presence of a solvent, for example, toluene, methanol or water to produce a diaryloxylated amine. The solvent is added in sufficient quantity to dissolve or disperse the reactants to insure better contact thereof.

Generally the primary amine and aromatic oxide are reacted at a pressure of from about atmospheric pressure to about 500 p.s.i.g. at a temperature of from 176° F. to 450° F., for 1 to 5 hours. The primary amine is preferably reacted with the aromatic oxide at a molar ratio of 1:2 to produce a diaryloxylated amine. It should be noted that aryloxylated amines herein include the aryl, alkylaryl and arylalkyl species of the amine, as well as the diaryloxylated forms. It may be desirable to react the primary amine with two different aromatic oxides to produce a mixed aryloxylated amine. In this embodiment of the invention, one mole of the primary amine is reacted with one mole each of two different aromatic oxides to produce the desired mixed oxide amine. Yet another method of producing the desired aryloxylated amine involves reacting one mole of an aromatic oxide and one mole of an alkene oxide, for example ethylene oxide, with a primary amine to produce a dioxylated amine having an aromatic moiety and an alkyl moiety attached to the nitrogen atoms of the primary amine.

Next, the diaryloxylated amine or mixed diaryloxylated amine is reacted with boric acid at a molar ratio of from about 1:2 to about 1:1 in the presence of a solvent, for example, xylene, benzene, toluene, or the like., to produce a boron containing heterocyclic compound of the present invention, i.e., a boramid compound. Normally, the solvent will comprise from about 20 to about 50 weight percent, preferably from about 30 to about 40 weight percent of the reaction mixture. The reaction is conducted under reflux at a temperature of from 176° F. to 450° F., preferably from 176° F. to 300° F., at a pressure of from atmospheric pressure to about 500 p.s.i.g. for about 1 to about 5 hours. The boramid compound thus produced will contain from about 0.5 to about 10 weight percent, preferably from about 2 to about 5 weight percent of boron.

Metal derivatives of the boron containing heterocyclic compounds, i.e., metal boramid compounds, herein are conveniently prepared by contacting a boramid compound with a metal usually in salt form. Thus, the metal acetates, propionates, etc., are suitable for use. The preferred metal compound for use in incorporating the metal ion into the boramid compound is the metal acetate. Generally, the boramid compounds are reacted with the metal compounds in a molar ratio range of from about 1:4 to about 6:1, preferably from about 1:1 to about 4:1, at a pressure of from about atmospheric to about 500 p.s.i.g. and a temperature of from about 176° F. to about 450° F.

Desirable metals are usually selected from transition metals having an atomic number of 21 through 30 or Group IVA metals of the Periodic Table. Transition metals which are suitable for use are selected from scandium, titanium, vanadium, chromium, manganese, iron, cobalt, nickel, copper and zinc and mixtures thereof. Suitable Group IVA metals include lead and tin and mixtures thereof. Normally, the metal will comprise from about 1 to about 17 weight percent, preferably from about 5 to about 9 weight percent of the boramid compound. When a metal is incorporated into the boramid compounds herein, the metal will displace and substitute for the hydrogen atom attached to the oxygen atom which is a component of the hydroxy group attached to the boron atom of the boramid structure.

Boron containing heterocyclic compounds prepared in accordance with the procedure herein have the following formula:

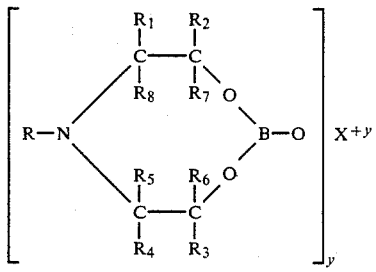

where R is hydrogen or an alkyl, alkene, alkadiene, aryl, alkylaryl or arylalkyl radical having from 1 to 24 carbon atoms, $R_1$, $R_2$, $R_3$ and $R_4$ are the same or different radicals selected from hydrogen or an alkyl, aryl, alkylaryl or arylalkyl radical having from 1 to about 30 carbon atoms, wherein at least one of said $R_1$, $R_2$, $R_3$ or $R_4$ is an aryl, alkylaryl or arylalkyl radical having from about 6 to about 30 carbon atoms, preferably at least two of said $R_1$, $R_2$, $R_3$ or $R_4$ is an aryl, alkylaryl or arylalkyl radical having from about 6 to about 30 carbon atoms, $R_5$, $R_6$, $R_7$ and $R_8$ are the same or different radicals selected from hydrogen or an alkyl group having from about 1 to about 6 carbon atoms, y is an integer between 1 and 4, and x is hydrogen or a metal selected from a transition metal having an atomic number of 21 through 30 or a Group IVA metal.

Preferably, at least one of $R_1$, $R_2$, $R_3$ or $R_4$ is an aryl, alkylaryl or arylalkyl radical having from about 6 to about 20 carbon atoms with the aryl species being especially preferred. Preferably $R_5$, $R_6$, $R_7$ and $R_8$ are hydrogen or an alkyl group having from 1 to about 4 carbon atoms. In an especially preferred mode, at least two of said $R_1$, $R_2$, $R_3$ or $R_4$ are aryl, alkylaryl or arylalkyl radicals having from about 6 to about 20 carbon atoms, and are preferably from 6 to 15 carbon atoms.

Representative heterocyclic, boramid compounds produced in accordance with the procedure herein include the following compounds: 1-hydroxy-3,7-diphenyl-5-dodecyl-5-aza-1-bora-2,8-dioxacyclooctane; 1-hydroxy-4,6-diphenyl-5-dodecyl-5-aza-1-bora-2,8-dioxacyclooctane; 1-hydroxy-4,7-diphenyl-5-dodecyl-5-aza-1-bora-2,8-dioxacyclooctane; 1-hydroxy-3,7-dicresyl-5-dodecyl-5-aza-1-bora-2,8-dioxacyclooctane; 1-hydroxy-4,6-dicresyl-5-dodecyl-5-aza-1-bora-2,8-dioxacyclooctane; 1-hydroxy-4,7-dicresyl-5-dodecyl-5-aza-1-bora-2,8-dioxacyclooctane; 1-hydroxy-3,7-dimethyl-3,7-diphenyl-5-dodecyl-5-aza-1-bora-2,8-dioxacyclooctane; 1-hydroxy-4,6-dimethyl-4,6-diphenyl-5-dodecyl-5-aza-1-bora-2,8-dioxacyclooctane; 1-hydroxy-4,7-dimethyl-4,7-diphenyl-5-dodecyl-5-aza-1-bora-2,8-dioxacyclooctane; 1-hydroxy-3 7-para tertiarybutylphenyl-5-dodecyl-5-aza-1-bora-2,8-dioxacyclooctane; 1-hydroxy-4,6-para tertiarybutylphenyl-5-dodecyl-5-aza-1-bora-2,8-dioxacyclooctane; 1-hydroxy-4,7-para tertiarybutylphenyl-5-dodecyl-5-aza-1-bora-2,8-dioxacyclooctane; 1-hydroxy-3,7-diphenyl-5-coco-5-aza-1-bora-2,8-dioxacyclooctane; and 1-hydroxy-3,7-diphenyl-5-tallow-5-aza-1-bora-2,8-dioxacyclooctane and mixtures thereof. It should be noted that the methyl, ethyl, propyl, butyl, cyclohexyl, octadecyl, phenyl, steryl, oleyl, coco and tallow moieties may be substituted for the dodecyl moiety in the above heterocyclic compounds.

Representative metallic derivatives of the above compositions include the following compounds: copper di[-1-oxy-3,7-diphenyl-5-dodecyl-5-aza-1-bora-2,8-dioxacyclooctane]; copper di[-1-oxy-4,6-diphenyl-5-dodecyl-5-aza-1-bora-2,8-dioxacyclooctane]; copper di[-1-oxy-4,7-diphenyl-5-dodecyl-5-aza-1-bora-2,8-dioxacyclooctane]; copper di[-1-oxy-3,7-dicresyl-5-dodecyl-5-aza-1-bora-2,8-dioxyacyclooctane]; copper di[-1-oxy-4,6-dicresyl-5-dodecyl-5-aza-1-bora-2,8-dioxacyclooctane]; copper di[-1-oxy-4,7-dicresyl-5-dodecyl-5-aza-1-bora-2,8-dioxacyclooctane]; copper di[-1-oxy-3,7-dimethyl-3,7-diphenyl-5-dodecyl-5-aza-1-bora-2,8-dioxacyclooctane]; copper di[-1-oxy-4,6-dimethyl-4,6-diphenyl-5-dodecyl-5-aza-1-bora-2,8-dioxacyclooctane]; copper di[-1-oxy-4,7-dimethyl-4,7-diphenyl-5-dodecyl-5-aza-1-bora-2,8-dioxacyclooctane]; copper di[-1-oxy-3,7-para tertiarybutylphenyl-5-dodecyl-5-aza-1-bora-2,8-dioxacyclooctane]; copper di[-1-oxy-4,6-para tertiarybutylphenyl-5-dodecyl-5-aza-1-bora-2,8-dioxacyclooctane]copper di[-1-oxy-4,7-para tertiarybutylphenyl-5-dodecyl-5-aza-1-bora-2,8-dioxacyclooctane]; copper di[-1-oxy-3,7-diphenyl-5-coco-5-aza-1-bora-2,8-dioxacyclooctane]; and copper di[-1-oxy-3,7-diphenyl- 5-tallow-5-aza-1-bora-2,8-dioxacyclooctane] and mixtures thereof. Other metals which may be incorporated into the above compounds, i.e., substituted for the copper, include scandium, titanium, vanadium, chromium, manganese, iron, cobalt, nickel, zinc, lead and tin and mixtures thereof. In addition, methyl, ethyl, propyl, butyl, cyclohexyl, octadecyl, phenyl, steryl, oleyl, coco and tallow moieties may be substituted for the dodecyl moiety in the above-described heterocyclic compounds.

The extreme pressure, anti-wear and friction reducing additives described herein may be incorporated in a wide variety of lubricating oils, for example, mineral oil, (including automobile engine oil), crude oil, synthetic oil, industrial oils, for example, cutting oil, metal working fluids and grease. For example, the additives may be added to lubricating oils derived from paraffins, naphthenic or mixed base crude petroleum oils, that have been subjected to solvent and/or sulfuric-acid treatment, aluminum chloride treatment, hydrogenation and/or other refining treatments. In addition, the additives described herein may be incorporated in petroleum distillates, such as diesel fuel, jet engine fuel, furnace oil, gas oil and other light oils. The petroleum oils may be of virgin or cracked petroleum stock, or mixtures thereof, boiling in the range of about 100° F. to about 1,100° F. The petroleum oil may contain cracked components such as those derived from cycle oils or cycle cuts boiling above gasoline, usually in the range of about 450° F. to about 750° F. and may be derived by catalytic or thermal cracking. Oils of high or low sulfur content such as diesel fuels or oils may additionally be used.

Preferred distillate lubrication oils which are improved by the addition of additives herein have an initial boiling point within the range of 350° F. to about 475° F., and end point in the range of about 500° F. to about 1,100° F., and a flash point not lower than 110° F.

Lubricants derived from oil shale are particularly desirable for use herein. Oil shale is broadly defined as a variety of compact sedimentary rock, generally laminated, that contains little or no oil but does contain organic material, derived from aquatic organisms or waxy spores and pollen grains, which is convertible to oil by heat. Crude shale oil, in combination with water, gas and spent shale containing a carbonaceous residue and mineral matter, is formed by the pyrolysis of oil shale. The hydrocarbons of shale oil are highly unsaturated, resembling the products of thermal cracking of petroleum, as would be expected because of the pyrolytic origin of shale oil. Once the shale oil is extracted, it is subjected to conventional hydrotreating procedures to produce a variety of hydrocarbon products, including lubricants.

Synthetic lubricating oils useful herein are those oils derived from a product of chemical synthesis (man-made oils). Typical examples of such compositions include the polyglycol fluids (i.e., polyalkylene glycol); silicones which consist of a silicone-oxygen polymer chain to which are attached hydrocarbon branches composed of either alkyl or phenyl groups; phosphates; polyphenyl esters; synthetic hydrocarbons and various esters of organic acids and alcohols.

The polyalkylene glycol lubricating oils suitable for use herein preferably are derived from the reaction product of the appropriate alkylene oxides. The alkylene moiety of the above compositions have a carbon chain of from about 1 to about 10 carbon atoms, preferably from about 200 to about 1,000, most preferably from about 200 to about 800. Representative examples of suitable polyalkylene glycols include, polyethylene glycol, polypropylene glycol, polyisopropylene glycol, polybutylene glycol and the like.

Synthetic lubricating oils derived from hydrocarbons are generally of two types, namely, dialkylated benzene and polymerized alpha-olefins. Dialkylated benzene herein is formed from the condensation product of the appropriate alkyl compound and has a carbon chain from about 5 to about 50 carbon atoms, preferably from about 8 to about 20 carbon atoms; and a molecular weight of from about 200 to about 1,500, preferably from about 300 to about 700. Representative compounds include di-n-decylbenzene, n-decyl-n-tetradecylbenzene, and n-nonyl-n-dodecylbenzene.

Alpha-olefins suitable for use in preparing lubricating oils herein are characterized by the formula $RCH=CH_2$ wherein R is a radical selected from the group of hydrogen and alkyl radicals having from about 4 to about 18 carbon atoms, preferably from about 6 to about 10 carbon atoms, and having a molecular weight of from about 80 to about 300, preferably from about 100 to about 200. Typical compounds include 1-octene, 1-decene and 1-dodecene.

Phosphates suitable for use herein as synthetic lubricating oils are the phosphate esters having the formula $O=P(OR)_3$, wherein R is aryl or alkyl having from about 4 to about 20 carbon atoms, preferably from 6 to about 10 carbon atoms, and have a molecular weight within the range of from about 200 to about 1,000, preferably from about 300 to about 550. Representative compounds include trioctyl phosphate, tricresyl phosphate and dicresyl methyl phosphate.

Esters of organic acids which are suitable for use herein as synthetic lubricating oils preferably are selected from organic acids having carbon chains of from $C_4$ to $C_{40}$ carbon units. Organic acids which may be reacted with the alcohols herein include caproic, decanoic, sebacic, laurel, oleic, stearic, palmitic, etc. Likewise, alcohols herein may be derived from either natural or synthetic origin, for example, pentaerythritol, trimethylolpropane, amyl, 2-ethylhexanol or laurel alcohol, may be used to form the desired ester. The esters are formed using conventional methods. For example, the esters may be prepared by reaction of the desired alcohol with the desired acid, acid anhydride or acid halide using conventional reaction conditions and techniques.

Preferably, the boron containing heterocyclic compounds, including metal derivatives thereof, are added to a lubricating oil at concentrations of from about 0.1 to about 15, especially from about 0.5 to about 10 weight percent of the lubricating oil-boramid blend. Alternatively, the heterocyclic compounds may be blended with suitable solvents to form concentrates that may readily be dissolved in the appropriate oil at the desired concentration. If a concentrate is employed, it ordinarily will contain at least 10 to about 90, preferably from 25 to about 75 weight percent of said heterocyclic compound. The solvent in such a concentrate may be present at levels of about 10 to about 90, especially from about 25 to about 50 weight percent of said concentrate. Suitable solvents which may be used for this purpose are naphtha and light mineral oil (i.e., 150 to 450 neutral oil) and mixtures thereof. The particular solvent selected should, of course, be selected so as not to adversely affect the other desired properties of the ultimate oil composition. Thus, the solvent used in incorporating the additive in a fuel oil should be compatible with the fuel in terms of stability, boiling range, corrosiveness, etc.

It should be noted, that it may be desirable to blend together two different heterocyclic compounds or metal derivatives thereof. Generally, when two different heterocyclic compounds are blended, a weight ratio of from about 1:20 to about 20:1, preferably from about 1:10 to about 10:1 is highly desirable for imparting extreme pressure, anti-wear and friction reducing properties to lubricating oils.

If desired, the extreme pressure, anti-wear and friction reducing additives described herein may be employed in conjunction with other additives commonly used in petroleum products. Thus, there may be added to the oil compositions of this invention rust and corrosion inhibitors, emulsifying agents, antioxidants, dyes, haze inhibitors, anti-static agents, detergents, dispersants, viscosity index improvement agents and pour point reducing agents. Soaps or other thickening agents may be added to the lubricating oil compositions to form compositions having the consistency of a grease. When other additives are employed, it may be desirable, although not necessary to prepare additive concentrates comprising concentrated solutions of the herein boron or metal-boron derivatives together with said other additives whereby the several additives are added simultaneously. Dissolution of the additive or additive concentrate into the oil composition may be facilitated by mixing accompanied with mild heating, but this is not absolutely essential.

The invention is further illustrated by the following examples which are illustrative of various aspects of the invention as defined by the appended claims.

EXAMPLE I

The boramid compound, 1-hydroxy-3,7-diphenyl-5-coco-5-aza-1-bora-2,8-dioxacyclooctane, is prepared by adding 14,889 grams of cocoamine[1] and 17,516 grams of styrene oxide to a 65 liter round bottomed flask that contains 13 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 34,373 grams of 1-hydroxy-3,7-diphenyl-5-coco-5-aza-1-bora-2,8-dioxacyclooctane.

[1]Cocoamine is a mixture of primary amines consisting of approximately 52 percent dodecylamine, 19 percent of tetradecylamine, 9 percent of hexadecyl amine, 6.5 percent of octylamine, 6 percent of decylamine, 2 percent of octadecyl amine and 5 percent of a mixture of octadecenylamine and octadecadienylamine. Cocoamine is produced commercially by the Armak Company under the tradename of Armeen CD.

EXAMPLE II

A boramid compound is prepared by adding 17,605 grams of tallowamine[2] and 15,362 grams of styrene oxide to a 65 liter round bottomed flask that contains 11.34 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product at a temperature of 400° F. The reaction produces 34,695 grams of 1-hydroxy-3,7-diphenyl-5-tallow-5-aza-1-bora-2,8-dioxacyclooctane.

[2]Tallowamine is a mixture of amines consisting of approximately 29 percent hexadecylamine, 20.5 percent octadecylamine, 44 percent of a mixture of octadecenylamine and octadecadienylamine, 3 percent tetradecylamine, 1.5 percent hexadecenylamine, 1 percent heptadecylamine and 0.5 percent tetradecenylamine. Tallowamine is produced commercially by the Armak Company under the tradename Armeen T.

EXAMPLE III

The boramid compound, 1-hydroxy-3,7-diphenyl-5-dodecyl-5-aza-1-bora-2,8-dioxacyclooctane, is prepared by adding 13,502 grams of dodecylamine and 17,516 grams of styrene oxide to a 65 liter round bottomed flask that contains 13.34 liters of toluene and 1 liter of water. The flask is placed in a heating mantle and fitted with a water-cooled condenser. The mixture thus formed is heated until it begins to reflux. Next, the temperature is adjusted to give a moderate reflux rate and the reaction mixture is refluxed for 24 hours. The reaction mixture is cooled to room temperature and 4,595 grams of boric acid are added to the flask. Then, the flask is equipped with a Dean-Stark trap topped with a water-cooled condenser and the reaction mixture is refluxed until water stops collecting in the trap. Toluene is distilled from the reaction product at a temperature of 400° F. The reaction produces 32,986 grams of 1-hydroxy-3,7-diphenyl-5-dodecyl-5-aza-1-bora-2,8-dioxacyclooctane.

EXAMPLE IV

The boramid compound, 1-hydroxy-4,6-dicresyl-5-dodecyl-5-aza-1-bora-2,8-dioxacyclooctane is prepared by adding 21 grams of boric acid with 61.7 grams of dodecylamine, 89.3 grams of para methylstyrene oxide and 250 ml of toluene to a single necked one liter round-bottomed flask. The toluene acts as a solvent and as an azeotrope for water produced during the reaction. It should be noted that boric acid is not soluble in toluene. The flask is placed in a heating mantle and fitted with a Dean Stark trap that is topped with a water-cooled condenser. The mixture thus formed is heated until it begins to reflux. Next, the mantle heat is adjusted to give a moderate reflux rate. The reaction mixture is refluxed for one hour, or until the stoichiometric amount of water (12 ml) collects in the Dean-Stark trap and all of the boric acid has dissolved, after which the toluene is distilled from the reaction product. The reaction produces 160 grams of product.

EXAMPLE V

The boramid compound, 1-hydroxy-3,7-dimethyl-3,7-diphenyl-5-dodecyl-5-aza-1-bora-2,8-dioxacyclooctane, is prepared by following the procedure of Example III with the following substitution:

Alpha methyl styrene oxide is substituted for the styrene oxide with substantially the same results.

EXAMPLE VI

Boric acid (21 grams), para tertiary-butyl styrene oxide (119.3 grams), dodecylamine (61.7 grams) and 250 ml of toluene are mixed in a one liter single-necked flask to prepare 1-hydroxy-4,6-para tertiarybutylphenyl-5- dodecyl-5-aza-1-bora-2,8-dioxacyclooctane. The flask is equipped with a heating mantle, Dean-Stark trap and water-cooled condenser. The mixture is heated under reflux until the reaction is completed; (12 ml) of water collects in the Dean-Stark trap. Next, toluene is distilled from the reaction mixture. The product thus prepared is suitable for use as an extreme pressure, anti-wear and friction reducing additive for lubricating compositions.

It should be noted that the other primary amines herein may be substituted for the dodecylamine above, to form the corresponding boramid compound.

EXAMPLE VII

A copper derivative of 1-hydroxy-3,7-diphenyl-5-coco-5-aza-1-bora-2,8-dioxacyclooctane is prepared by following the procedure of Example I with the following exception: the above-described compound (47 grams), 100 ml of toluene, 20 ml of triethyl amine and 10 grams of cupric acetate are mixed in a single-necked, 500 ml round bottom flask, equipped with a heating mantle, Dean-Stark trap and water-cooled condenser. The mixture is refluxed for 16 hours, then filtered and the toluene, amine, water and acetic acid (produced in situ) are distilled from the reaction product. Using the above-procedure, copper di[-1-oxy-3,7-diphenyl-5-dodecyl-5-aza-1-bora-2,8-dioxacyclooctane] is produced.

It is to be noted that other transition metals having an atomic number from 21 to 30, and Group IVA metals of the periodic table may be substituted for the copper metal herein to prepare corresponding metal derivatives of the above compound.

EXAMPLE VIII

A nickel derivative of 1-hydroxy-4,6-diphenyl-5-coco-5-aza-1-bora-2,8-dioxacyclooctane is prepared by following the procedure of Example VII with the following exception:

nickel acetate is substituted for the cupric acetate. The reaction produces nickel di[-1-oxy-3,7-diphenyl-5-coco-5-aza-1-bora-2,8-dioxacyclooctane].

EXAMPLE IX

Lead di[-1-oxy-3,7-diphenyl-5-coco-5-aza-1-bora-2,8-dioxacyclooctane] is prepared in accordance with the procedure of Example I with the following exception:

The reaction product produced in Example I (23.5 grams), 100 ml of toluene, 9.5 grams of lead acetate and 100 ml of triethylamine are mixed in a single-necked 500 ml round bottom flask, equipped with a water-cooled condenser and heating mantle and Dean-Stark trap. The mantle heat is adjusted until a moderate rate of reflux is obtained. The mixture thus formed is refluxed for 18 hours. Next, the mixture is filtered, toluene, water, triethylamine and acetic acid (produced in the reaction) are distilled from the reaction product. The reaction produces lead di[-1-oxy-3,7-diphenyl-5-dodecyl-5-bora-2,8-dioxacyclooctane].

EXAMPLE X

Iron di[-1-oxy-3,7-diphenyl-5-coco-5-aza-1-bora-2,8-dioxyacyclooctane] is prepared according to the procedure of Example I with the following exception:

a mixture comprising 23.5 grams of the reaction product produced in Example I, 100 ml of toluene, 4.3 grams of ferrous acetate and 100 ml of triethylamine are introduced into a single-necked 500 ml round bottom flask, equipped with Dean-Stark trap, water-cooled condenser and heating mantle. The heating mantle is adjusted to give a moderate rate of reflux of the reaction mixture. The mixture is refluxed for 18 hours. Next, the mixture is filtered and the triethylamine, toluene, and acetic acid (produced in the reaction) are distilled from the reaction product.

EXAMPLE XI

A boramid compound is prepared by adding 17,093 grams of octadecylamine and 15,362 grams of styrene oxide to a 65 liter round bottomed flask that contains 13 liters of toluene and 1 liter of water. The flask is fitted with a water-cooled condenser and placed in a heating mantle. The mixture thus formed is refluxed at a moderate rate for 24 hours. The reaction is cooled to room temperature and 4,033 grams of boric acid are added to the flask. Next, the flask is fitted with a Dean-Stark trap, topped with a water-cooled condenser and the reaction mixture is refluxed until water stops collecting in the trap. Toluene is distilled from the reaction product at a temperature of 400° F. The reaction produces 34,183 grams of 1-hydroxy-3,7-diphenyl-5-octadecyl-5-aza-1-bora-2,8-dioxacyclooctane.

EXAMPLE XII

The procedure of Example XI is followed to produce 1-hydroxy-3,7-diphenyl-5-phenyl-5-aza-1-bora-2,8-dioxacyclooctane with the following exception:

Phenylamine is substituted for octadecylamine.

EXAMPLE XIII

Zinc di[-1-oxy-3,7-diphenyl-5-coco-5-aza-1-bora-2,8-dioxacyclooctane] is produced according to the procedure of Example VII except that zinc acetate is substituted for the cupric acetate.

EXAMPLE XIV

Tin di[-1-oxy-3,7-diphenyl-5-coco-5-aza-1-bora-2,8-dioxacyclooctane] is prepared by substituting tin acetate for the cupric acetate in Example VII.

EXAMPLE XV

Lead di[-1-oxy-4,6-diphenyl-5-dodecyl-5-aza-1-bora-2,8-dioxacyclooctane] is prepared in accordance with the procedure of Example III with the following exception:

The reaction product produced in Example III (23.95 grams), 100 ml of toluene, 9.5 grams of lead acetate and 100 ml of triethylamine are mixed in a single-necked 500 ml round bottom flask, equipped with a water-cooled condenser, heating mantle and Dean-Stark trap. The mantle heat is adjusted until a moderate rate of reflux is obtained. The mixture thus formed is refluxed for 18 hours. Next, the mixture is filtered and the toluene, triethylamine, water and acetic acid (produced in-situ) are distilled from the reaction product. The reaction produces lead di[-1-oxy-3,7-dimethyl-3,7-diphenyl-5-dodecyl-5-aza-1-bora-2,8-dioxacyclooctane].

EXAMPLE XVI

A nickel derivative of 1-hydroxy-4,6-dicresyl-5-dodecyl-5-aza-1-bora-2,8-dioxacyclooctane is prepared by following the procedure of Example XV with the following exception:

paramethyl styrene oxide is substituted for styrene oxide and nickel acetate is substituted for lead acetate. The reaction produces nickel di[-1-oxy-3,7-dicresyl-5-dodecyl-5-aza-1-bora-2,8-dioxacyclooctane].

EXAMPLE XVII

Iron di[-1-oxy-3,7-diparatertiarybutyl-phenyl-5-dodecyl-5-aza-1-bora-2,8-dioxacyclooctane] is prepared according to the procedure of Example VI with the following exception:

a mixture comprising 28.4 grams of the reaction product produced in Example VI, 100 ml of toluene, 4.3 grams of ferrous acetate and 100 ml of triethylamine are introduced into a single-necked 500 ml round bottom flask, equipped with Dean-Stark trap, water-cooled condenser and heating mantle. The heating mantle is adjusted to give a moderate rate of reflux of the reaction mixture. The mixture is refluxed for 18 hours, filtered, and the toluene, triethylamine, water and acetic acid (produced in-situ) are distilled from the reaction product.

EXAMPLE XVIII

Zinc di[-1-oxy-3,7-diphenyl-5-dodecyl-5-aza-1-bora-2,8-dioxacyclooctane] is produced according to the procedure of Example XV except that zinc acetate is substituted for lead acetate.

EXAMPLE XIX

Tin di[-1-oxy-3,7-diphenyl-5-dodecyl-5-aza-1-bora-2,8-dioxacyclooctane] is prepared by substituting tin acetate for lead acetate in Example XV.

EXAMPLES XX TO XXVI

Extreme pressure, anti-wear and friction reducing additives produced according to the procedure of Examples I, VII, IX, X, XIII, and XIV are mixed with separate portions of 450 neutral oil at concentrations of 2 weight percent.

Each lubricant composition is tested in accordance with the procedure disclosed in ASTM:D3233-73 (Reapproved 1978) using a Falex lubricant tester. The test, in accordance with the above ASTM designation, is performed by applying resistance to a revolving metal journal. A rachet mechanism movably attached to two V-blocks applies resistance by steadily increasing pressure on the journal. The metal journal and V-blocks (steel) are submerged in the lubricant composition to be tested. A summary of the results obtained is disclosed in Table 1 below:

EXAMPLES XXVII AND XXVIII

The extreme pressure, anti-wear and friction reducing additive produced in accordance with the procedure of Example I is mixed at a concentration of 2 weight percent with SAE 30 motor oil which contains 0.05 weight percent phosphorus. A sample of the SAE 30 motor oil which does not contain the additive of Example I is used as a control.

Each lubricant composition is tested in accordance with the procedure disclosed in ASTM D3233-73 (Reapproved 1978) using a Falex lubricant tester. A summary of the results is disclosed in Table 2 below.

TABLE 2

| | TORQUE ON JOURNAL (LBS.-IN.) | |
| --- | --- | --- |
| | Example | |
| True Load Lbs. | XXIV Control (SAE 30 Motor Oil) | XXV SAE 30 Motor Oil With Additive of Ex. I |
| 300 | 9 | 8 |
| 500 | 14 | 12 |
| 750 | 20 | 17 |
| 950 | Journal Shear | — |
| 1,000 | — | 22 |
| 1,250 | — | 28 |
| 1,400 | — | Journal Shear |

The extreme pressure property of SAE 30 motor oil is substantially enhanced in Table 2 above when 2 weight percent of 1-hydroxy-3,7-diphenyl-5-coco-5-aza-1-bora-2,8-dioxacyclooctane is added to said SAE 30 motor oil.

Various embodiments and modifications of this invention have been described in the foregoing description and examples, and further modifications will be apparent to those skilled in the art. Such modifications are included within the scope of the invention as defined by the following claims.

We claim:

1. A compound having the formula:

TABLE 1

| | TORQUE ON JOURNAL (LBS.-IN) | | | | | | |
| --- | --- | --- | --- | --- | --- | --- | --- |
| | | Example | | | | | |
| True Load lbs | XX (450 Neutral Oil) | XXI Oil With Additive of Ex. I | XXII Oil With Additive of Ex. VII | XXIII Oil With Additive of Ex. IX | XXIV Oil With Additive of Ex. X | XXV Oil With Additive of Ex. XIII | XXVI Oil With Additive of Ex. XIV |
| 300 | 9 | 7 | 11 | 9 | 10 | 9 | 7 |
| 500 | 12 | 9 | 15 | 15 | 15 | 14 | 9 |
| 750 | Journal Shear | 17 | 21 | 21 | 22 | 22 | 16 |
| 990 | — | — | — | — | — | Journal Shear | — |
| 1,000 | — | 24 | 28 | 30 | 28 | — | 19 |
| 1,050 | — | — | Journal Shear | Journal Shear | Journal Shear | — | 23 |
| 1,250 | — | Journal Shear | — | — | — | — | 26 |
| 1,500 | — | — | — | — | — | — | Journal Shear |
| 1,750 | | | | | | | |

The above data indicate that the boron containing heterocyclic compounds described above impart extreme pressure properties to 450 neutral oil at concentrations of 2 weight percent.

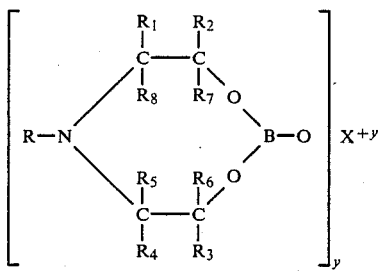

where R is hydrogen or an alkyl, alkene, alkadiene, aryl, alkylaryl or arylalkyl radical having from 1 to about 24 carbon atoms, $R_1$ and $R_4$ are the same or different radicals selected from hydrogen or alkyl, aryl, alkylaryl or arylalkyl radicals or a mixture thereof, said radicals having from 1 to about 30 carbon atoms, $R_2$ and $R_3$ are the same or different aryl, alkylaryl or arylalkyl radicals having from about 6 to about 30 carbon atoms, $R_5$, $R_6$, $R_7$, and $R_8$ are the same or different radicals selected from hydrogen or an alkyl radical having from 1 to about 6 carbon atoms, Y is an integer between 1 and 4, and X is hydrogen or a metal selected from a transition metal having an atomic number of 21 through 30 or a Group IVA metal.

2. A compound having the formula:

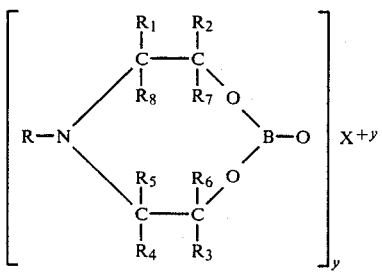

where R is an alkyl, alkene, alkadiene, aryl, alkylaryl or arylalkyl radical having from 1 to about 24 carbon atoms, $R_1$, and $R_4$ are the same or different radicals selected from hydrogen or an alkyl, aryl, alkylaryl or arylalkyl radicals having from 1 to about 30 carbon atoms, $R_2$ and $R_3$ are the same or different aryl, alkylaryl or arylalkyl radicals having from about 6 to about 30 carbon atoms, $R_5$, $R_6$, $R_7$ and $R_8$ are the same or different radicals selected from hydrogen or an alkyl radical having from 1 to about 6 carbon atoms, Y is an integer between 1 and 4, and X is hydrogen or a metal selected from a transition metal having an atomic number of 21 through 30 or a Group IVA metal.

3. The compound defined in claim 2 wherein R is an alkyl, alkene, alkadiene, aryl, alkylaryl or arylalkyl radical having from 1 to about 18 carbon atoms.

4. The compound defined in claim 2 or 3 wherein $R_1$ and $R_4$ are the same or different radicals selected from hydrogen or alkyl, aryl, alkylaryl or arylalkyl radicals having from 1 to about 20 carbon atoms, and $R_2$ and $R_3$ are aryl or arylalkyl radicals having from about 6 to about 20 carbon atoms.

5. The compound defined in claims 2 or 3 wherein $R_2$ and $R_3$ are the same aryl radical having 6 carbon atoms.

6. The compound defined in claims 1 or 2 wherein X is a metal selected from the group consisting of scandium, titanium, vanadium, chromium, manganese, iron, cobalt, nickel, copper, zinc, tin and lead and mixtures thereof.

7. The compound defined in claims 1 or 2 wherein said compound contains from about 0.5 to about 10 weight percent of boron.

8. The compound defined in claims 1 or 2 wherein said compound contains from about 1 to about 17 weight percent of a transition metal having an atomic number from 21 to 30 or a Group IVA metal.

9. A process for producing a boron-containing heterocyclic compound having the formula:

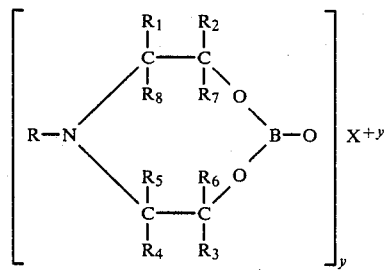

where R is hydrogen or an alkyl, alkene, alkadiene, aryl, alkylaryl or arylalkyl radical having from 1 to about 24 carbon atoms, $R_1$ and $R_4$ are the same or different radicals selected from hydrogen or alkyl, aryl, alkylaryl or arylalkyl radicals having from 1 to about 30 carbon atoms, $R_2$ and $R_3$ are the same or different aryl, alkylaryl or arylalkyl radicals having from about 6 to about 30 carbon atoms, $R_5$, $R_6$, $R_7$, and $R_8$ are the same or different radicals selected from hydrogen or an alkyl radical having from 1 to about 6 carbon atoms, Y is an integer between 1 and 4, and X is hydrogen or a metal selected from a transition metal having an atomic number of 21 through 30 or a Group IVA metal, which comprises:

(A) contacting a primary amine or ammonia with an aromatic oxide of the formula:

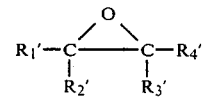

wherein at least one of said $R_1'$, $R_2'$, $R_3'$ or $R_4'$ is aryl, alkylaryl or arylalkyl with the remaining R groups being independently hydrogen or an organic radical having 1 to 30 carbon atoms to produce a reaction product; and (B) contacting the reaction product of step (A) with boric acid to produce said boron-containing heterocyclic compound.

10. The process defined in claim 9 wherein the contacting in step (A) is with a primary amine selected from the group consisting of methylamine, ethylamine, propylamine, butylamine, octadecylamine, cyclohexylamine, dodecylamine, phenylamine, oleylamine, cocoamine and tallowamine and mixtures thereof.

11. The process defined in claim 9 wherein the aromatic oxide is a member selected from the group consisting of styrene oxide, alpha methyl styrene oxide, para tertiary butyl styrene oxide, ortho methyl styrene oxide and para methyl styrene oxide and mixtures thereof.

12. The process defined in claim 9 wherein a primary amine and an aromatic oxide are contacted in step (A) at a molar ratio of 1:2 to produce said reaction product.

13. The process defined in claim 9 wherein the reaction product and boric acid are contacted at a molar ratio of from 1:2 to 1:1 to produce a boron containing heterocyclic compound.

14. The process defined in claim 13, including contacting the boron containing heterocyclic compound with a metal selected from either a transition metal having an atomic number of 21 to 30 or a Group IVA metal or a mixture thereof.

15. The process defined in claim 14 wherein the transition metal or Group IVA metal is a member selected from the group consisting of scandium, titanium, vanadium, chromium, manganese, iron, cobalt, nickel, copper, zinc, tin and lead and mixtures thereof.

16. The process defined in claim 14 wherein the boron-containing heterocyclic compound and the metal are contacted at a molar ratio of from about 1:4 to about 6:1.

17. The process defined in claim 14 wherein the boron-containing heterocyclic compound and metal are contacted at a temperature of from about 176° F. to about 450° F. and a pressure of from atmospheric pressure to about 500 p.s.i.g.

18. A process for producing a boron-containing heterocyclic compound having the formula:

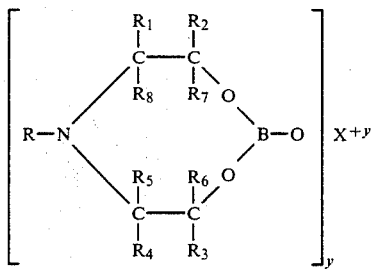

where R is an alkyl, alkene, alkadiene, aryl, alkylaryl or arylalkyl radical having from 1 to about 24 carbon atoms, $R_1$ and $R_4$ are the same or different radicals selected from hydrogen or alkyl radicals having from 1 to about 6 carbon atoms, $R_2$ and $R_3$ are the same or different aryl, alkylaryl or arylalkyl radicals having from 6 to about 30 carbon atoms, $R_5$, $R_6$, $R_7$, and $R_8$ are the same or different radicals selected from hydrogen or an alkyl radical having from 1 to about 6 carbon atoms, Y is an integer between 1 and 4, and X is hydrogen or a metal selected from a transition metal having an atomic number of 21 through 30 or a Group IVA metal, which comprises:

(A) contacting a primary amine with an aromatic oxide of the formula:

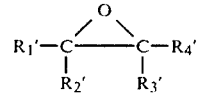

wherein at least one of said $R_1'$, $R_2'$, $R_3'$ or $R_4'$ is aryl, alkylaryl or arylalkyl with the remaining R groups being independently hydrogen or an alkyl radical having 1 to 6 carbon atoms to produce a reaction product; and (B) contacting the reaction product of step (A) with boric acid to produce said boron-containing heterocyclic compound.

19. The process defined in claim 10, 12, 13, 14, 15, 16 or 18 wherein the aromatic oxide comprises styrene oxide.

20. The process defined in claim 18 wherein the aromatic oxide is a member selected from the group consisting of styrene oxide, alpha methyl styrene oxide, para tertiary butyl styrene oxide, ortho methyl styrene oxide and para methyl styrene oxide and mixtures thereof.

21. The process defined in claim 18, including the further step of contacting the boron-containing heterocyclic compound with a metal selected from either a transition metal having an atomic number of 21 to 30 or a Group IVA metal and mixtures thereof.

22. The process defined in claim 21 wherein the transition metal or Group IVA metal is a member selected from the group consisting of scandium, titanium, vanadium, chromium, manganese, iron, cobalt, nickel, copper, zinc, tin and lead or a mixture thereof.

23. The process defined in claim 21 wherein the boron containing heterocyclic compound and the metal are contacted at a molar ratio of from 1:4 to 6:1.

24. The process defined in claim 21 wherein the boron-containing heterocyclic compound and metal are contacted at 176° F. to about 450° F. and a pressure of from atmospheric pressure to about 500 p.s.i.g.

* * * * *